United States Patent [19]

Lipson et al.

[11] Patent Number: 4,710,623

[45] Date of Patent: Dec. 1, 1987

[54] OPTICAL FIBER CATHETER WITH FIBER-CONTAINED REACTIVE ELEMENT

[75] Inventors: David Lipson; Benjamin L. Liu; Nicolas G. Loebel, all of Indianapolis, Ind.

[73] Assignee: Eli Lilly and Company, Indianapolis, Ind.

[21] Appl. No.: 833,245

[22] Filed: Feb. 27, 1986

[51] Int. Cl.[4] .............................................. H01J 5/16
[52] U.S. Cl. ...................................... 250/227; 128/634
[58] Field of Search ........................... 250/227, 231 R; 350/96.1; 128/634

[56] References Cited

U.S. PATENT DOCUMENTS

| Re. 31,879 | 5/1985 | Lubbers et al. | 436/133 |
|---|---|---|---|
| 3,123,066 | 3/1964 | Brumley | 128/634 |
| 4,344,438 | 8/1982 | Schultz | 128/634 |
| 4,357,106 | 11/1982 | Tschirren et al. | 356/44 |
| 4,476,870 | 10/1984 | Peterson et al. | 128/634 |
| 4,560,248 | 12/1985 | Cramp et al. | 350/96.34 |

OTHER PUBLICATIONS

Continuous Measurement of Intravascular pH with a Fiberoptic Sensor, Anesthesia & Analgesia Journal, vol. 64, pp. 731-736, publ. date 1985.

Primary Examiner—David C. Nelms
Assistant Examiner—Chung K. Seo
Attorney, Agent, or Firm—Barnes & Thornburg

[57] ABSTRACT

An elongated optical fiber apparatus for transmitting a light signal toward a first end of the apparatus situated within a fluid to be analyzed, and for transmitting a returning light signal that is indicative of a specified characteristic of the fluid toward a second end of the apparatus that is situated outside the fluid. The optical fiber apparatus includes a light conductive cable capable of transmitting light with a hole formed in its first end. Disposed substantially entirely within this hole is a reactive element that reacts with the fluid to alter a property of the light that is indicative of a specified characteristic of the fluid.

20 Claims, 16 Drawing Figures

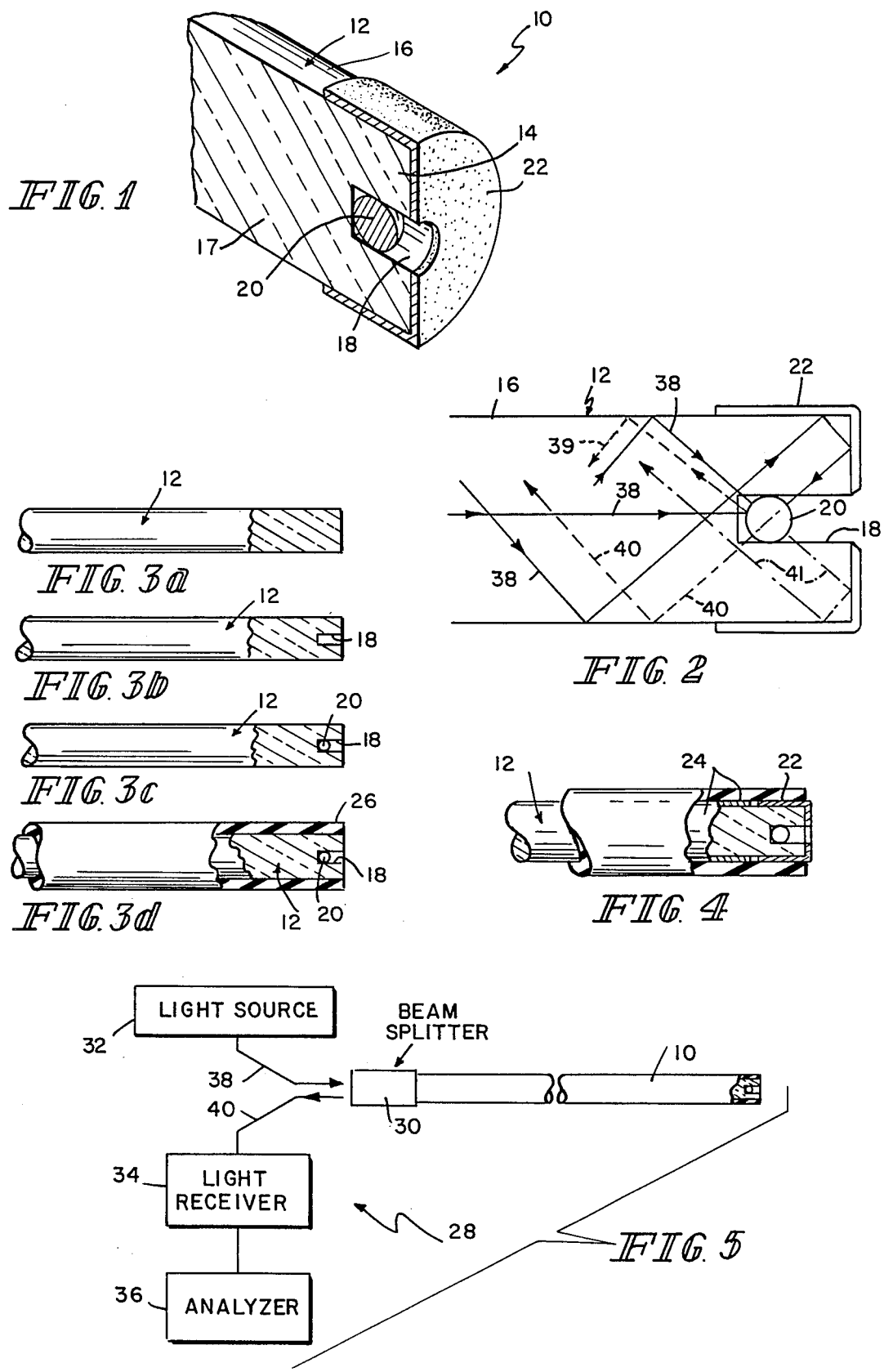

OPTICAL FIBER CATHETER WITH FIBER-CONTAINED REACTIVE ELEMENT

The present invention relates to an optical fiber apparatus for transmitting an incident light signal toward a first end, and for transmitting a returning light signal toward a second end that is indicative of a specified characteristic of the environment in which the first end is positioned. More particularly, the present invention relates to an optical fiber apparatus for insertion into a fluid to be analyzed to measure a specified characteristic of that fluid.

Known sensing systems using optical fibers to transmit light indicative of a specified characteristic of a fluid have generally had a chamber attached to the end of the optic cable. This chamber normally contains one or more receptor sites for interacting with the fluid to be analyzed. The chamber interior is normally isolated from the fluid by a selectively porous membrane. This membrane is designed to allow the particular constituent of the fluid that is to be analyzed to enter the interior of the chamber, and to exclude all other unwanted portions. Examples of known sensing systems are found in U.S. Pat. Nos. 4,357,106; 4,344,438; and Re 31,879.

One problem with the known sensing systems of the type described is that the chamber attached to the end of the optic cable is prone to physical damage. Such known chambers are delicate because they are situated as an external appendage located on the end of the optic cable. Any mishandling of the cable can easily result in damage to the delicate chamber.

Another problem with the known sensing systems is that the chamber is difficult to attach securely to the end of the cable. Many of the sensing systems are designed to be used as a catheter for insertion into a blood vessel of a body. This use as a catheter requires that the chamber be extremely small. The small size of the chamber makes attachment to the small optic cable very difficult. Furthermore, the failure of secure attachment leads to the chamber becoming disengaged from the optic fiber, with obvious problems resulting.

One object of the present invention is to provide an optical fiber apparatus for transmitting an incident light signal toward a first end, and for transmitting a returning light signal toward a second end that is indicative of a specified characteristic of the contents of a fluid that overcomes the deficiencies of the prior art.

Another object of the present invention is to provide an optical fiber apparatus that does not require a reactive chamber to be attached to the end of the optic cable, thereby eliminating any chance of damage to the chamber.

Still another object of the present invention is to provide an optical fiber apparatus that eliminates the problems associated with attaching a chamber to the end of the optic cable.

According to the present invention, an optical fiber apparatus is provided for transmitting an incident light signal toward the first end of the apparatus which is situated inside a fluid. The apparatus also carries a returning signal toward a second end that is situated outside the fluid. The returning signal is indicative of a specified characteristic of the contents of the fluid. The apparatus includes a light conductive cable capable of transmitting light, with a hole formed in the first end of the cable. A reactive element is inserted totally into the hole in the end of the cable. The reactive element reacts with the fluid being analyzed to alter a property of the returning light as compared to the incident light. The returning light is thereby indicative of a specified characteristic of that fluid.

In some preferred embodiments of the present invention, the first end of the cable may be coated with a selectively or highly reflective material. One advantage of the reflective coating is that more incident light is reflected through the reactive element and transmitted toward the second end of the cable.

Also in preferred embodiments of the present invention, substantially the entire surface of the cable is coated with a protective sheath. One advantage of the protective sheath is that the cable is better adapted to be used as a catheter for insertion into a blood vessel in a body. Another advantage of the protective sheath is that more light is transmitted through the cable because the protective sheath tends to prevent light loss from the cable.

Also in preferred embodiments of the present invention, the hole in the end of the cable is formed by a method that is fast and accurate, such as, for example, by laser machining, microdrilling, or by chemical etching. One advantage of this method of forming the hole is that the hole is accurately formed. Another advantage of this method is that a multiplicity of cables can be so formed in succession, and to identical specifications, thus permitting the cables to be mass-produced.

Also in preferred embodiments of the present invention, the reactive elements consist of specific binding agents (e.g. antibodies) for a ligand of interest, possibly in combination with a ligand analog. For example, a ligand analog may consist of a ligand labeled with a fluorescent substance whereby a change in the quantum yield of said label occurs when ligand analog is bound to the specific binding agent. In the presence of non-labeled ligand (provided by the fluid being analyzed) the ligand analog is competitively displaced from the specific binding agent, resulting in a change in the emission intensity.

One feature of the present invention is that the reactive element is contained entirely within the hole in the operative end of the cable. One advantage of this feature is that the reactive element is protected from possible damage through contact with foreign objects. Another advantage of this feature is that the cable has a uniform diameter throughout its length. The reactive element, by not being fixed to the outer surface of the cable, does not create an area of increased diameter at the sensing tip. This allows the cable to be wholly encased within a smooth biocompatible coating, thereby reducing the chance of thrombogenicity which could otherwise occur. This permits the cable to be more easily used as a catheter, especially in the smaller sized blood vessels.

In one embodiment of the present invention, the first end of the cable is planar, with the plane being orthogonal to the longitudinal axis of the cable, and the hole extends axially inwardly into the cable and is concentric with the outer circumference of the cable. However, the apparatus of the present invention is not limited to this configuration of either the hole, or the first end of the cable.

For example, the hole need not be either radially or axially symmetrical with respect to the outer circumference of the cable. Thus, the hole may be formed in the first end of the cable such that it is not centrally located in the first end, and the hole may extend inwardly at an angle to the longitudinal axis of the cable. Also, more than one hole may be formed in the first end of the cable with a different reactive element placed in each hole.

The first end of the cable may also be planar, with the plane at an angle other than 90° to the longitudinal axis of the cable. With this configuration, the hole may be in the first end with its axis parallel to the longitudinal axis of the cable, or the hole may be in the outer surface of the cable, near the first end, with its axis perpendicular to the longitudinal axis of the cable. The hole may also be in the form of an annular, circumferentially extending channel in the outer surface of the cable near the first end.

Furthermore, the first end of the cable may be frusto-conically shaped, or parabolically shaped, with the hole extending axially inwardly with its axis parallel to the longitudinal axis of the cable.

Additional objects, features, and advantages of the invention will become apparent to those skilled in the art upon consideration of the following detailed description of preferred embodiments exemplifying the best mode of carrying out the invention as presently perceived. The detailed description particularly refers to the accompanying figures in which:

FIG. 1 is an isometric view in section of the optical fiber apparatus;

FIG. 2 is a diagrammatic illustration of the optical fiber apparatus schematically showing a path of travel of the light;

FIGS. 3a-3d are side views with portions broken away of the ends of the optical fiber apparatus illustrating the steps of forming the optical fiber apparatus;

FIG. 4 is a side view with portions broken away illustrating the final step of forming the optical fiber apparatus using a modified optic cable;

FIG. 5 is a diagrammatic illustration of an optical fiber sensing system including the optical fiber apparatus of FIG. 1;

Figure 6:
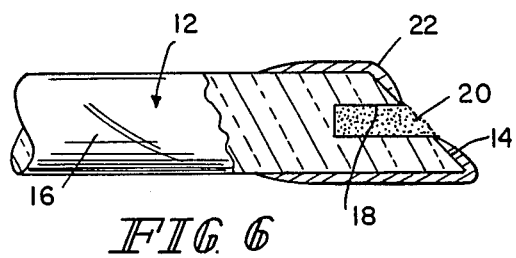
FIG. 6 is a side view with portions broken away of the end of the optical fiber apparatus illustrating one modification.

Referring now to the drawings, an optical fiber apparatus 10 is shown in FIG. 1. The optical fiber apparatus 10 includes an optical cable 12 capable of transmitting light. The optical cable 12 has a first end 14 that is planar and oriented to be perpendicular to the longitudinal axis of the cable 12. The optical cable 12 also has an outer surface 16 and an inner core 17. The core 17 is lined for glass but can be constructed of any material which would function as required to achieve the necessary optical performance.

A hole 18 is formed in the center of the first end 14 of the cable 12, either by laser machining, by microdrilling, or by other equivalent means such that the hole 18 is generally concentric with the circumference of the first end 14. Illustratively, the hole 18 has a diameter approximately one-third the diameter of the cable 12. The depth of the hole 18 is approximately equal to the diameter of the hole 18.

A reactive element 20 is inserted into the hole 18. The reactive element 20 is contained totally within the hole 18. The hole 18 may optionally be covered with a semipermeable membrane (not shown) whose porosity is chosen so as to confine the reactive element 20 within the hole 18 and prevent the admission into the hole 18 of substances larger than the analyte. As shown, the reactive element 20 is spherical shaped. The size of the reactive element can range from several hundred angstroms to several microns. It is understood that the reactive element 20 may have other shapes including being a disperse matrix of a polymer or a liquid, with the restriction being that the entire reactive element is preferably contained totally within the hole 18.

A reflective coating 22 may be layered over the first end 14 of the cable 12, with the reflective coating 22 extending axially inwardly from the first end 14 over a portion of the outer surface 16 of the cable 12 The reflective coating 22 is required when light will pass through the reactive element 20 and be reflected from the first end 14 of the cable 12 (absorbance). The reflective coating 22 is helpful where the reactive element 20 absorbs and retransmits the light (fluorescence). The reflective coating 22 is not used when light is reflected off of the reactive element 20 toward the second end of the cable 12 (light-scattering). The reflective coating 22 may be layered directly over the outer surface 16, as shown in FIG. 1, or, if the optic cable 12 has an outer fiber jacket 24, as shown in FIG. 4, the outer fiber jacket 24 may be stripped back, and the reflective coating 22 layered over the exposed inner core 17 of the cable 12. The reflective coating 22 should not cover hole 18 as the reactive element 20 would be prevented from reacting with the fluid environment in which the first end is situated.

In addition, the reflective coating 22 may be constructed to be wavelength specific, whereby certain wavelengths of light are reflected and others allowed to be transmitted out of the first end 14. This significantly improves the ability of the system to quantify the desired information by reducing or eliminating wavelengths of light passing through but not interacting with the reactive element 20. The reflective coating 22 may be made wavelength specific by using conventional optical filtering techniques.

The optical fiber apparatus 10 can be prepared in the following manner. Referring to FIGS. 3a, 3b, 3c, and 3d, it is first assumed that a reflective coating 22 is not to be used. The optic cable 12 is microdrilled to form the hole 18, as shown in FIG. 3b. The reactive element 20 is then placed in the hole 18 so that the reactive element 20 is contained totally within the hole 18, as shown in FIG. 3c. A protective sheath 26 is then applied over substantially the entire outer surface 16 of the cable 12, as shown in FIG. 3d, to protect the apparatus 10. If the optical fiber apparatus 10 is to be used as a catheter for insertion into the body, the protective sheath 26 is chosen for its biocompatibility as well as its protective ability. The selection of suitable materials is within the skill of persons familiar with body invasive instrumentation.

If the reflective coating 22 is to be applied to the cable 12, the reflective coating 22 is applied as a first step before the cable 12 is microdrilled. If it is necessary to strip off the outer fiber jacket 24, the stripping is performed first, with the reflective coating 22 then applied, followed by the step of microdrilling. The steps described previously, subsequent to the microdrilling, would remain the same, whether a reflective coating 22 is used or not.

Referring now to FIG. 5, an optical fiber sensing system 28 is shown. The sensing system 28 25 includes the optical fiber apparatus 10, a beam splitter 30, a light source 32, a light receiver 34, and an analyzer 36.

In operation, the optical fiber apparatus 10 portion of the sensing system 28 is inserted into the body, for example, a blood vessel of the body, in a conventional manner. The reactive element 20 interacts with the contents of the body, which for illustrative purposes will be considered to be blood in a blood vessel of the body. This interaction between the blood and the reactive element 20 changes a specific property of the reactive element 20 in a conventional manner, the reaction of which is not part of the present invention. The reactive element 20 is chosen such that changes in the specific characteristic of the blood, or other fluid that is to be analyzed, will be indicated by changes in the property of the reactive element 20.

Incident light 38 from the light source 32 passes through the beam splitter 30, and is transmitted in a conventional manner toward the first end 14 of the optic fiber 12, as best shown in FIG. 5. As the incident light 38 nears the first end 14 of the optic fiber 12, the optional reflective coating 22 functions to minimize any loss of the incident light 38 through the first end 14.

Referring now to FIG. 2, the incident light 38 may be reflected by the reflective coating 22, and travel through the hole 18 and contained reactive element 20. In addition, the incident light 38 may be reflected from the reactive element 20 or may be absorbed by, and retransmitted from, the reactive element 20 at a wavelength generally equal to or greater than that of the incident light 38, corresponding to the well-known phenomena of absorbance, light-scattering, and fluorescence. As the incident light 38 passes through the reactive element 20, or is reflected from the reactive element 20, or is absorbed by and retransmitted from the reactive element 20, a property of the light 38 is altered in a conventional manner.

The amount of alteration or change in a property of the incident light 38 is dictated by the change in the property of the reactive element 20 as it interacts with the blood, or other fluid of the body, as described previously. Thus, the change in the incident light 38 is a function of the reaction between the reactive element 20 and the fluid to be analyzed. As discussed previously, this reaction between the reactive element 20 and the fluid is indicative of a specific characteristic of the fluid. Therefore, the change in the incident light 38 is indicative of the specific characteristic of the fluid to be analyzed.

The altered incident light 38 is transmitted away from the first end 14 of the cable 12, and will be referred to as the returning light 39, 40, 41, as shown in FIG. 2. Returning light 39 represents the light that is reflected from the reactive element 20. Returning light 40 represents the light that passes through the reactive element 20. Returning light 41 represents the light that is absorbed by, and retransmitted from, the reactive element 20 at a wavelength equal to or greater than that of the incident light 38. It will be understood that the returning light 39, 40, 41 may also include a portion of the incident light 38 that is reflected from the reflective coating 22 if the reflective coating 22 is applied to the first end 14 of the cable 12.

Referring now to FIG. 5, the returning light 40 passes through the beam splitter 30, which separates the incident light 38 from the returning light 40 in a conventional manner. The returning light 40 then passes through the light receiver 34 to the analyzer 36. The analyzer 36 compares the returning light 40 with the incident light 38 in a conventional manner, and measures the desired specific characteristic of the fluid. It is understood that the present invention is not limited to use inside the body. The fluid to be tested, for example blood, may be withdrawn from the body conventionally, and the optical fiber apparatus 10 used to analyze this drawn blood. The specific characteristic may be, but is not limited to, the presence of drugs, level of metabolites, pressure, temperature and dissolved gases.

Referring now to FIGS. 6–13, possible modifications of the invention are shown. FIG. 6 shows the optic cable 12 having a planar first end 14, with the plane being at an angle other than 90° with respect to the longitudinal axis of the cable 12, for example, at the polarizing angle. The hole 18 is concentric with the circumference of the outer surface 16 of the cable 12, and extends longitudinally inwardly. The reactive element 20 is shown as a disperse element disposed within the hole 18, rather than as a spherical element as shown in FIGS. 1 and 2.

Figure 7:
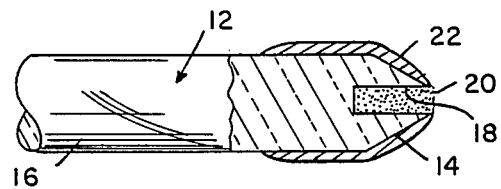
FIG. 7 is a side view with portions broken away of the end of the optical fiber apparatus illustrating another modification to the optical fiber apparatus.

FIG. 7 shows the optic cable 12 having a frustoconical shaped first end 14. The hole 18 is concentric with the circumference of the outer surface 16 of the cable 12 and extends longitudinally inwardly.

Figure 8:
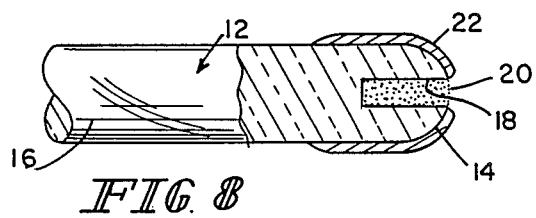
FIG. 8 is a side view with portions broken away of the end of the optical fiber apparatus illustrating another modification to the optical fiber apparatus.

FIG. 8 shows the optic cable 12 having a parabolically shaped first end 14. The hole 18 is concentric with the circumference of the outer surface 16 of the cable 12 and extends longitudinally inwardly.

Figure 9:
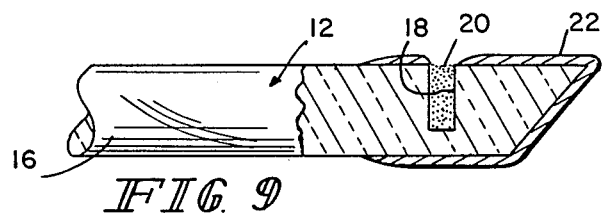
FIG. 9 is a side view with portions broken away of the end of the optical fiber apparatus illustrating another modification to the optical fiber apparatus.

FIG. 9 shows the optic cable 12 having a planar first end 14, with the plane being at an angle other than 90° with respect to the longitudinal axis of the cable 12, similar to the cable 12 shown in FIG. 6. However, the hole 18 extends radially inwardly from the outer surface 16 at a location near the first end 14.

Figure 10:
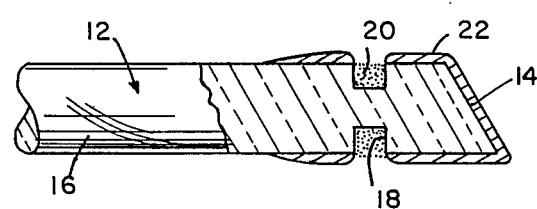
FIG. 10 is a side view with portions broken away of the end of the optical fiber apparatus illustrating another modification to the optical fiber apparatus.

FIG. 10 shows the optic cable 12 having a planar first end 14, with the plane being at an angle other than 90° with respect to the longitudinal axis of the cable 12. The hole 18 in this embodiment is an annular groove that extends circumferentially around the optic cable 12 and extends radially inwardly from the outer surface 16 of the cable 12.

Figure 11:
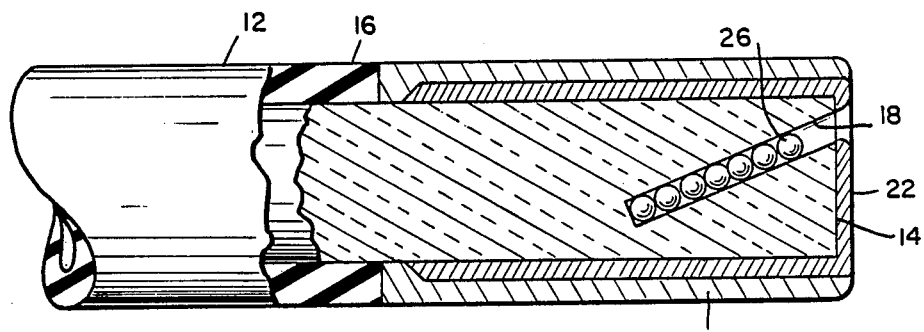
FIG. 11 is a side view with portions broken away of the end of the optical fiber apparatus illustrating another modification to the optical fiber apparatus.

FIG. 11 shows the optic cable 12 having a planar first end 14, with the plane being substantially perpendicular to the longitudinal axis of the cable 12. The hole 18 in the first end 14 extends through the reflective coating 22 and is not concentric with the outer surface 16 of the cable 12 and extends inwardly at an angle to the longitudinal axis of the cable 12. An abrasion-resistant coating 60 is shown covering the reflective coating 22. The abrasion-resistant coating 60 is designed to protect the first end 14 and the reflective coating 22. The abrasion-resistant coating 60 is chosen for its biocompatibility as well as for its protective ability.

Figure 12:
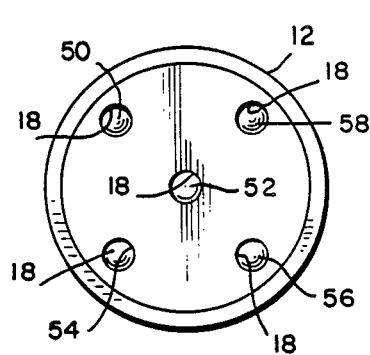
FIG. 12 is an end view of the optical fiber apparatus illustrating another modification to the optical fiber apparatus.
Figure 13:
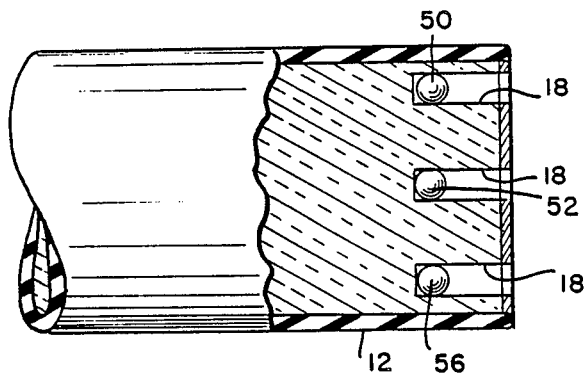
FIG. 13 is a side view with portions broken away of the end of the optical fiber apparatus of FIG. 12.

FIGS. 12 and 13 show the optic cable 12 having a planar first end 14, with the plane being substantially perpendicular to the longitudinal axis of the cable 12. Five holes 18 are formed in the first end 14, with the holes spaced about the surface of the first end 14. The five holes 18 are provided to allow different types of reactive elements, illustratively reactive elements 50, 52, 54, 56, 58, to be included in the optic cable 12. Each reactive element 50, 52, 54, 56, 58 produces a different interaction with the incident light 38, thereby enabling the light receiver 34 and the analyzer 36 to spectrally analyze more than one characteristic of the body contents at the same time using only a single optic cable 12. It will be understood that the light source 32, the light receiver 34, and the analyzer 36 will necessarily be more complex components because of the requirement to demultiplex the information in the returning light 39, 40, 41.

The modifications of the invention shown in FIGS. 6-13 each have specific characteristics that may be advantageous, depending on the type of fluid to be analyzed, and other factors such as the type of incident light 38 used. It is understood that there are numerous factors that could affect the choice of the particular modification that is best suited for a given use.

Although the invention has been described in detail with reference to a preferred embodiment and specific examples, variations and modifications exist within the scope and spirit of the invention as described and defined in the following claims.

We claim:

1. An elongated optical fiber apparatus for transmitting an incident light signal toward a first end of the apparatus, the first end situated in a fluid, and for transmitting a returning light signal toward a second end of the apparatus that is indicative of a specified characteristic of the fluid, the second end being situated outside the fluid, the apparatus comprising:
    a light-conductive cable containing only a single optical fiber capable of transmitting light;
    a hole formed in the first end of the single fiber;
    a reactive element inserted into said hole to react with the contents of the fluid to alter a property of the light that is indicative of a specified characteristic of the fluid.

2. The apparatus of claim 1 further comprising a coating of a reflective material applied to the first end of the cable.

3. The apparatus of claim 2, wherein the reflective coating is wavelength specific to permit certain wavelengths of the light signal to be reflected by the reflective coating and other wavelengths to pass through the reflective coating.

4. The apparatus of claim 1 wherein substantially the entire surface of said cable is coated with a protective sheath.

5. The apparatus of claim 1 wherein the cable has a central, longitudinal axis and the hole extends axially inwardly into said single fiber from said first end and is centered about the central axis of the cable.

6. The apparatus of claim 1 wherein the cable has a central, longitudinal axis and the hole has a central, longitudinal axis and the hole extends radially inwardly from the outer surface of said cable near said first end such that the central axis of the hole is substantially perpendicular to the central axis of the cable.

7. The apparatus of claim 1 wherein said hole is an annular channel extending circumferentially around the outer surface of said cable near the first end.

8. The apparatus of claim 1 wherein said first end of the cable is planar, and said cable has a central, longitudinal axis, and wherein an angle defined by said first end of the able and said central axis of the cable is orthogonal.

9. The apparatus of claim 1 wherein said first end of the cable is planar, and said cable has a central, longitudinal axis, and wherein an angle defined by said first end of the cable and said central axis of the cable is non-orthogonal.

10. The apparatus of claim 9 wherein said angle defined by said first end of the cable and said central axis of the able is the polarizing angle.

11. The apparatus of claim 1, wherein said first end of the cable is frustoconically shaped.

12. The apparatus of claim 1 wherein said first end of the cable is parabolically shaped.

13. A method of making an optical fiber apparatus for insertion into a fluid for transmitting an incident light signal toward a first end of the apparatus, the first end to be situated inside the fluid, and for transmitting a returning light signal toward a second end of the apparatus that is indicative of a specified characteristic of the fluid, the second end to be situated outside the fluid, comprising the steps of:
    providing a light-conductive cable containing only a single otpical fiber having a first end;
    forming a hole in said first end of the optical fiber;
    filling said hole with a reactive agent to react with the fluid to alter a property of the returning light that is indicative of a specified characterized of the fluid; and
    forming a protective sheath around substantially the entire surface of the cable.

14. The method of claim 13 wherein the light-conductive cable has an outer jacket and further including the step of stripping a portion of said outer jacket from the cable near the first end.

15. The method of claim 14 further including the step of applying a reflective coating to said stripped portion of the cable.

16. The method of claim 13 further including the step of applying a reflective coating to said first end of the cable and a portion of the surface of the cable near the first end.

17. Method of claim 13 wherein the hole forming step is performed by laser machining.

18. The method of claim 13 wherein the hole forming step is performed by microdrilling.

19. The method of claim 13 further comprising the step of covering the hole with a semi-permeable membrane whose porosity is chosen to confine the reactive agent within the hole while permitting transport of an analyte.

20. The method of claim 13 further comprising the step of dispersing the reactive agent in a polymeric matrix prior to said filling step.

* * * * *